United States Patent [19]

Kondo et al.

[11] Patent Number: 6,011,170
[45] Date of Patent: Jan. 4, 2000

[54] PROCESS FOR PRODUCING OF CYSTEINE DERIVATIVES

[75] Inventors: Takeshi Kondo, Takasago; Akira Nishiyama; Noboru Ueyama, both of Kobe; Hiroshi Murao; Hajime Manabe, both of Takasago; Yasuyoshi Ueda, Himeji, all of Japan

[73] Assignee: Kaneka Corporation, Osaka, Japan

[21] Appl. No.: 09/142,688

[22] PCT Filed: Jan. 14, 1998

[86] PCT No.: PCT/JP98/00101

§ 371 Date: Apr. 22, 1999

§ 102(e) Date: Apr. 22, 1999

[87] PCT Pub. No.: WO98/30538

PCT Pub. Date: Jul. 16, 1998

[30] Foreign Application Priority Data

Jan. 14, 1997 [JP] Japan ................................ 9-017342

[51] Int. Cl.[7] .................................................. C07C 321/04
[52] U.S. Cl. ........................... 560/147; 560/152; 562/557
[58] Field of Search ............................ 562/557; 560/147, 560/152

[56] References Cited

U.S. PATENT DOCUMENTS 5,516,936  5/1996  Phillips et al. ........................... 562/430

OTHER PUBLICATIONS

Liebigs Ann. Chem., (6), 1988, p5010505, Wulff et al., 'Uber die Darstellung von N–(Arylmethylen)dehydroalanin–methylestern sowie ihre Eignung als Bausteine in der Aminosauresynthese.'.

Database Casereact, An. No. 109:23350, Wulff et al., 'Synthesis of N–(Arnymethylene)dehydroalanine methyl esters and their application as building blocks in the synthsis of amino acids.' Liebigs Ann. Chem., (1988), (6), p501–505 (abstract).

J. Org. Chem., 1990, 55, p3998–4006, Hermkens et al., 'Intramolecular Pictet–Spengler Reaction of N–Alkoxytryptamines. 3. Stereoselective Synthesis of (–)–Debromoeudistomin L and (–)–O–Methyldebromoeudistomin E and Their Stereoisomers.'.

Primary Examiner—Gary Geist
Assistant Examiner—Brian J. Davis
Attorney, Agent, or Firm—Pollock, Vande Sande & Amernick

[57] ABSTRACT

This invention relates to a method comprising reacting an amino acid derivative of the following general formula (I);

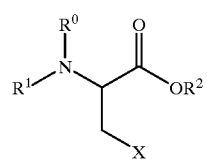

(I)

(wherein $R^1$ represents an amino-protective group; $R^0$ represents hydrogen or, taken together with $R^1$, represents an amino-protecting group; $R^2$ represents a carboxy-protecting group; X represents a leaving group) with a thiol compound of the following general formula (II):

$R^3SH$  (II)

(wherein $R^3$ represents an alkyl group of 1 to 7 carbon atoms, an aryl group of 6 to 10 carbon atoms, or an aralkyl group of 7 to 10 carbon atoms) to give a cysteine derivative of the following general formula (III):

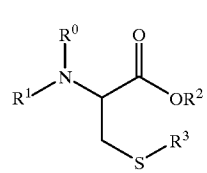

(III)

(wherein $R^0$, $R^1$, $R^2$, and $R^3$ are as defined above), wherein the reaction is conducted in the presence of a base and water in an organic reaction solvent.

23 Claims, No Drawings

PROCESS FOR PRODUCING OF CYSTEINE DERIVATIVES

TECHNICAL FIELD

The present invention relates to a process for producing a cysteine derivative of the following general formula (III) (hereinafter referred to as cysteine derivative (III)).

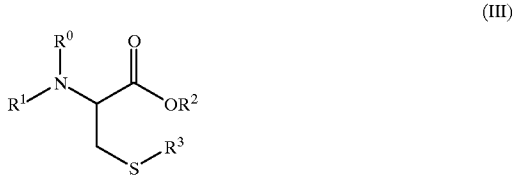
(III)

(wherein $R^1$ represents an amino-protecting group; $R^0$ represents hydrogen or, taken together with $R^1$, represents an amino-protecting group; $R^2$ represents a carboxy-protecting group; $R^3$ represents an alkyl group of 1 to 7 carbon atoms, an aryl group of 6 to 10 carbon atoms, or an aralkyl group of 7 to 10 carbon atoms.)

The cysteine derivative (III) which can be provided by the present invention is a compound of importance as a starting material for intermediates of an HIV-protease inhibitor and, according to WO 96/23756 and EP 604185A1, for instance, is of value as a starting material for the reaction according to the following schema.

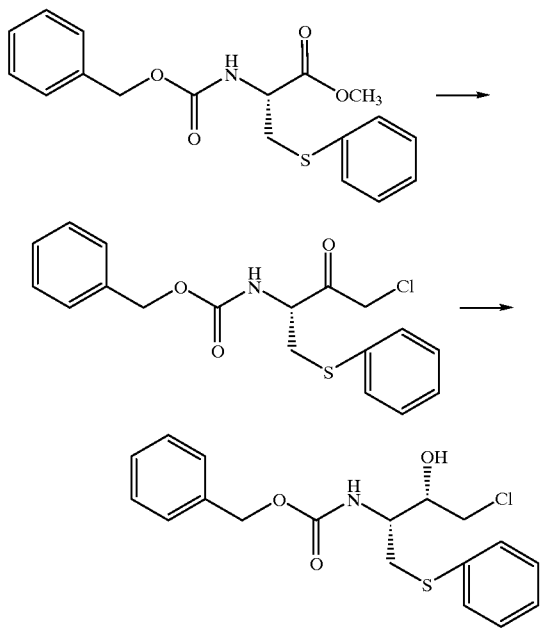

BACKGROUND ART

For the production of the above cysteine derivative (III), there is already known the technology by which an $R^3$–S group is introduced into a compound whose amino and carboxyl groups have been protected, for example the process which comprises transforming the hydroxyl group of a serine derivative Into a leaving group and then conducting a substitution reaction [Tetrahedron Letters, 28, 6069 (1987), ibid, 34, 6607 (1993), and EP 604185A1].

However, this technology involves transformation of the hydroxyl group of a serine derivative into a sulfonyloxy group and a subsequent substitution reaction with the sodium salt of a thiol in anhydrous N,N-dimethylformamide. None of the available literature refer to the impurity by-produced in the reaction, but our investigation revealed that, in this reaction, there is a problem that the sodium salt of thiol or its derivatives, which acts as a base, causes abstraction of the carbonyl α-hydrogen and subsequent E2 elimination in competition with the objective substitution reaction to give the dehydroalanine derivative of the following general formula (IV) [hereinafter referred to as dehydroalanine derivative (IV)], with the result that the yield of the objective compound is decreased.

We also found that, when the objective cysteine derivative (III) is an optically active compound, a Michael addition of the thiol to the dehydroalanine derivative (IV) so produced may further cause the objective cysteine derivative (III) to reduce the optical purity thereof.

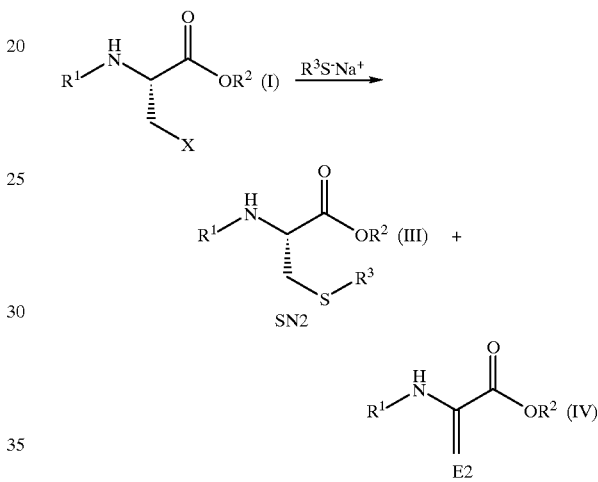

In the above reaction scheme, $R^1$, $R^2$, and $R^3$ are as defined above; X represents a leaving group.

Furthermore, as a production method of the thiol salt for use in the reaction, a method using sodium hydride or potassium hydride under anhydrous conditions have been used but, from the standpoint of handling, the method cannot be said to be suitable for industrial application.

Under the circumstances, the present invention has for its object to provide a process for producing a cysteine derivative, which is economical, high in production efficiency even in a commercial operation, and especially insuring a high optical purity of the objective compound.

SUMMARY OF THE INVENTION

The present invention is essentially directed to a method of producing a cysteine derivative which comprises reacting an amino acid derivative of the following general formula (I):

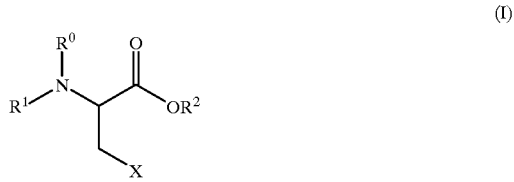
(I)

(wherein $R^0$, $R^1$, $R^2$ and X are as defined hereinbefore) with a thiol compound of the following general formula (II):

$$R^3SH \quad (II)$$

(wherein $R^3$ is as defined hereinbefore) in an organic reaction solvent in the presence of a base and water to give a cysteine derivative (III).

DETAILED DISCLOSURE OF THE INVENTION

The present invention is now described in detail.

In accordance with the invention, an amino acid derivative of the above general formula (I) [hereinafter referred to as amino acid derivative (I)] is reacted with a thiol compound of the above general formula (II) [hereinafter referred to as thiol compound (II)] to provide said cysteine derivative (III).

As defined above, said $R^1$ represents an amino-protecting group. If there is an effect that the amino group can be masked against the intended substitution reaction, this amino-protecting group is not particularly restricted to any specific group. Thus, a suitable amino-protecting group can be selected from among, for example, the protective groups described in PROTECTIVE GROUPS IN ORGANIC SYNTHESIS, Second Edition, John Wiley & Sons, 1991. From the standpoints of the ease of handling and availability at low cost, benzyloxycarbonyl, t-butoxycarbonyl, methoxycarbonyl, or ethoxycarbonyl is preferred.

Said $R^0$ is usually a hydrogen atom but when the amino-protecting group is phthaloyl, for instance, $R^0$, taken together with $R^1$, represents an amino-protecting group.

Said $R^2$ represents a carboxy-protecting group. If there is an effect that the carboxyl group can be masked against the substitution reaction, the carboxy-protecting group is not particularly restricted to any specific group. Thus, a suitable carboxy-protecting group can be selected from among, for example, the protective groups described In the document mentioned above with reference to $R^1$. For example, ester-forming protective groups are preferred, and lower alkyl, benzyl, and substituted benzyl are particularly preferred.

X represents a leaving group. This leaving group is not particularly restricted, either, but includes alkylsulfonyloxy group of 1 to 10 carbon atoms such as mesyloxy etc.; arylsulfonyloxy group of 6 to 10 carbon atoms such as tosyloxy etc.; aralkylsulfonyloxy group of 7 to 10 carbon atoms; acetyloxy, trihaloacetyloxy, and phosphoryl group of the following general formula (V):

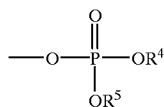

(V)

(wherein $R^4$ and $R^5$ each represents alkyl group of 1 to 10 carbon atoms, aryl group of 6 to 10 carbon atoms, or aralkyl group of 7 to 10 carbon atoms). From the standpoint of the ease of preparation and availability at low cost, tosyloxy and mesyloxy are preferred.

The base for use is not restricted in kind but, from practical points of view, an unexpensive base is preferably used. Thus, for example, such bases as hydroxides, carbonates, bicarbonates, acetates, hydrogenphosphates, and pH buffers can be mentioned. As counter cations, metal species such as lithium, sodium, and potassium or ammonium ion and the like can be mentioned. From the standpoint of improved SN2 reaction selectivity and/or for practical reasons, sodium hydroxide, sodium bicarbonate, potassium bicarbonate, and pH buffers and the like are preferred.

The amount of the base is at least 1 molar equivalent, preferably 1 to 2 molar equivalents, based on 1 molar of said amino acid derivative (I), and as will be described hereinafter, is preferably selected so that the reaction pH will be fall within the range of 3 to 11.

The thiol compound (II) is not particularly restricted in kind but includes alkyl mercaptans in which alkyl group contains 1 to 7 carbon atoms, aryl-mercaptans in which aryl group contains 6 to 10 carbon atoms, and aralkyl-mercaptans in which aralkyl group contains 7 to 10 carbon atoms. Preferred are methylmercaptan and phenylmercaptan.

Although the reaction temperature varies with the objective compound, it may be within the range not causing solidification of the reaction mixture. From the standpoint of selectivity for SN2 reaction, the reaction temperature is preferably not higher than 50° C. and more preferably within the range of 0 to 30° C.

The reaction time depends on the other conditions used but is generally 1 to 30 hours.

Since a prolonged reaction time does not appreciably detract from optical purity, satisfactory results can be obtained even if the reaction time exceeds 10 hours, for instance.

The reaction pH is selected in view of the pKa of the thiol compound (II) and the stability of the protective groups in said amino acid derivative (I) but is preferably within the range where the thiol compound may be available as a stable thiol salt in the reaction system, e.g. not below pH 3. Moreover, in order to secure a high selectivity for SN2 reaction, the pH is preferably not over 11. In the practice of this invention, the pH is maintained preferably within the range of 3 to 11, more preferably within the range of 3 to 10, throughout the entire course of the reaction. Since, with the progress of the reaction, the pH shifts toward the acidic side, the initial pH is preferably set on the alkaline side.

Besides, since the thiol compound (II) for use in the present Invention gives rise to a byproduct disulfide on oxidation and still the formation of this byproduct tends to be accelerated in the high pH range, the reaction is preferably carried out in an inert gas such as nitrogen gas. Moreover, for the purpose of suppressing the above formation of the byproduct disulfide, the reaction may be conducted in a comparatively low pH slot of the preferred pH range mentioned above, or depending on cases, may be conducted in the presence of an antioxidant of the common kind.

The organic reaction solvent for use in the present invention can be classified according to the following modes of use.

(1) A mode of use of an organic reaction solvent which gives a homogeneous phase with water (2) A mode of use of an organic reaction solvent which gives a heterogeneous phase with water The reaction system described above is valid for whichever of the above two modes.

In mode (1), the reaction is carried out in the presence of a base and water in an organic reaction solvent which gives a homogeneous phase with water.

The amount of water is not particularly restricted. However, in order to maintain a practically acceptable reaction velocity, the amount of water is preferably not more than 5 times the amount of the organic reaction solvent on a volume-to-volume basis Moreover, when the starting amino acid derivative (I) is an optically active compound composed predominantly of the D-form or the L-form, the amount of water is preferably not less than 1/50 times the amount of the organic reaction solvent on a volume-to-volume basis in order to inhibit the decrease in optical purity due to E2 elimination and subsequent Michael addition of thiol compound (II). Thus, the amount of water is preferably ⅟₅₀ to 5 times the amount of the organic reaction solvent on a volume-to-volume basis. Usually, the range of ⅟₂₀ to 5 volumes is selected.

This organic reaction solvent is not particularly restricted to any specific solvent only if it is an organic solvent giving a homogeneous phase with water. Thus, for example, ketones such as acetone etc.; ethers such as tetrahydrofuran etc.: and highly polar aprotic solvents such as acetonitrile, N,N-dimethylformamide, dimethyl sulfoxide, etc. can be mentioned. Those solvents can be used each alone or in a combination of 2 or more different species. Particularly when the starting amino acid derivative (I) is an optically active compound composed predominantly of the D-form or the L-form, on organic solvent containing at least one of N,N-dimethylformamide and dimethyl sulfoxide is preferred from the standpoint of inhibiting the decrease in optical purity.

The preferred reaction procedure in mode (1) is now described.

For the purpose of inhibiting the side reaction between said base and said amino acid derivative (I), it is generally recommendable, in mode ①, to cause said thiol compound (II) to react with said base to give the corresponding thiol salt in the first place.

This salt is then reacted with said amino acid derivative (I). This reaction can be carried out by, for example, (1) the method which comprises adding a solution of said salt of thiol compound (II) slowly to a solution of said amino acid derivative (I) or ② the method which comprises adding said amino acid derivative (I) or said solution of amino acid derivative (I) to said solution of said salt of thiol compound (II) and, in either case, a satisfactory result can be obtained.

The solvent for use in preparing the above-mentioned solution of amino acid derivative (I) may be the organic reaction solvent mentioned above or a mixture of the organic reaction solvent with water. The solvent which can be used for the preparation of said solution of the salt of thiol compound (II) may be water or a mixture of water with the organic reaction solvent.

The method of producing a cysteine derivative in mode (2), the method which comprises conducting the reaction in the presence of a base and water and in an organic reaction solvent which gives a heterogeneous phase with water as now described, The volumetric ratio of water to the organic reaction solvent is preferably 1:100 through 10:1 for all practical purposes. The kind and amount of the base which can be used are the same as those mentioned hereinbefore.

Above-mentioned organic reaction solvent for use in this mode is not particularly restricted to any specific solvent only provided that it is an organic solvent which gives a heterogeneous phase with water. Thus, for example, halogenated hydrocarbons such as methylene chloride, chlorobenzene, dichlorobenzene, etc.; esters such as ethyl acetate etc.; and ketones such as methyl isobutyl ketone etc. can be employed. Those solvents can be used each alone or in a combination of two or more different species. Particularly when the starting amino acid derivative is an optically active compound composed predominantly of the D-form or the L-form, halogenated hydrocarbons such as methylene chloride, chlorobenzene, and dichlorobenzene are preferred because they contribute to a higher selectivity for SN2 reaction.

Furthermore, in mode (2), a phase transfer catalyst can be used with advantage.

The phase transfer catalyst mentioned above is not particularly restricted but a variety of catalysts such as ammonium salts and phosphonium salts can be employed. From practical standpoints, such as the ease of availability, cost, and suitable reaction velocity or the like, it is preferable to use at least one member selected from the class consisting of benzyltributylammonium chloride, tetrabutylammonium hydrogensulfate, trioctylmethylammonium chloride, and tetrabutylphosphonlum bromide.

The reaction procedure in mode (2) may for example be ① the procedure which comprises adding a solution of said salt of thiol compound (II) either to a solution of said amino acid derivative (I) or to a solution containing said amino acid derivative (I) and phase transfer catalyst, ② the procedure which comprises adding said base or a solution thereof, either to a solution containing said amino acid derivative (I) and thiol compound (II) or to a solution containing said amino acid derivative (I), thiol compound (II), and phase transfer catalyst; or ③ the procedure which comprises adding said amino acid derivative (I) or a solution thereof either to a solution containing said thiol compound (II) and said base or to a solution containing said thiol compound (II), said base, and said phase transfer catalyst. In any of such cases, a satisfactory result can be obtained.

The solvent for use in the preparation of said solution of amino acid derivative (I) may for example be the organic reaction solvent mentioned above or r mixture of the organic reaction solvent with water. and the solvent for use in the preparation of said solution of the salt of thiol compound (II) may for example be water or a mixture of water with the organic reaction solvent. The solvent for use in the preparation of said solution containing amino acid derivative (I) and thiol compound (II) may for example be the organic reaction solvent or a mixture of the organic reaction solvent with water. The solvent which can be used for the preparation of said solution of the base may for example be water or a mixture of water with the organic reaction solvent. The solvent for use in the preparation of said solution containing thiol compound (II) and base may for example be water or a mixture of water with the organic reaction solvent.

The objective compound thus produced, viz. cysteine derivative (III), can be isolated by the routine procedure, such as extraction and crystallization.

The amino acid derivative (I) can be prepared typically by Introducing the leaving group x into the OH group of a serine derivative of the following general formula (VI) [hereinafter referred to as serine derivative (VI)].

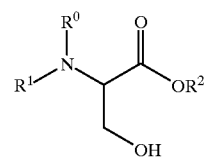

(VI)

(wherein $R^1$ represents an amino-protecting group; $R^0$ represents hydrogen or, taken together with $R^1$, represents an amino-protecting group; $R^2$ represents a carboxy-protecting group.) On this introduction of the leaving group, the use of the corresponding acid chloride is preferable. For example, alkylsulfonyl chlorides, e.g. methanesulfonyl chloride, tosyl chloride, arylsulfonyl chlorides, aralkylrulfonyl chlorides, acetyl chloride, trihaloacetyl chlorides, etc. can be mentioned.

The solvent which can be used in this case is not particularly restricted, and either a single solvent or a mixed solvent can be employed. The organic reaction solvent for use in the present invention can also be used in this procedure. Particularly when the serine derivative (VI) is an optically active compound composed predominantly of the D-form or the L-form, it is preferable to use a solvent containing at least one member selected from the class consisting of methylene chloride, toluene, and chlorobenzene in order to suppress the decrease in optical purity and inhibit side reactions.

When the combination of the leaving group, thiol compound, and solvent is a particular one, for example when the leaving group is mesyloxy, the thiol compound (II) is thiophenol. and the solvent is a solvent containing at least one member selected from the class consisting of methylens chloride, toluene, and chlorobenzene, the procedure of introducing the leaving group into the serine derivative (VI) and then reacting the derivative with the thiol compound (II) to give the cysteine derivative (III) can be performed without isolation of the amino acid derivative (I).

Since the method of producing a cysteine derivative according to the invention uses a base which is inexpensive and easy to handle and is capable of inhibiting side reactions and insuring a high SN2 reaction selectivity, thus leading to an improved yield of the objective compound, it is a commercially meritorious production technology. Furthermore, in the production of an optically active cysteine derivative (III), the decrease of optical purity can be precluded.

BEST MODE FOR CARRYING OUT THE INVENTION

The following examples are intended to illustrate the present invention in further detail and should by no means be construed as defining the scope of the invention.

In the examples, the optical purity of N-benzyloxycarbonyl-S-phenyl-L-cysteine methyl ester was analyzed by using an optical isomer isolation HPLC column (CHIRAL PAK AD, Daicel Chemical) and the SN2 and E2 reaction selectivity ratio was calculated by means of the following equation.

Reaction selectivity = $SN2$ reaction: $E2$ reaction =

$$(L-D)/(L+D+A):(D\times2+A)/(L+D+A)$$

where L represents the yield of N-benzyloxycarbonyl-S-phenyl-L-cysteine methyl ester, D represents the yield of N-benzyloxycarbonyl-S-phenyl-D-cysteine methyl ester; and A represents the yield of N-benzyloxycarbonyldehydroalanine methyl ester.

EXAMPLE 1

Under nitrogen gas at room temperature, 3.62 ml of 1N-sodium hydroxide/H$_2$O was added to 411 mg of thiophenol and the mixture was stirred for 30 minutes. Then, 5 ml of N,N-dimethylformamide was added and the solution was cooled to about 0° C. To this solution was added 971 mg of N-benzyloxycarbonyl-O-mesyl-L-serine methyl ester (hereinafter referred to as mesyl compound) with the aid of 10 ml of N,N-dimethylformamide, and the reaction was conducted for 22 hours. Analysis of this reaction mixture by HPLC revealed that the yield of N-benzyloxycarbonyl-S-phenyl-L-cysteine methyl ester (hereinafter referred to as S-phenyl-L-cysteine derivative) was 937 mg (93%), the yield of N-benzyloxycarbonyl-S-phenyl-D-cysteine methyl ester (hereinafter referred to as S-phenyl-D-cysteine derivative) was 56 mg (5%), and the optical purity was 88.8% ee. Moreover, the yield of N-benzyloxycarbonyl dehydroalanine methyl ester (hereinafter referred to as dehydroalanine derivative) was 0.4% and SN2:E2 =88:12.

EXAMPLE 2

Under nitrogen gas at room temperature, 15 ml of distilled water and 885 mg of sodium bicarbonate were added to 1277 mg of thiophenol and the mixture was stirred for 30 minutes. Then, 10 ml of N,N-dimethylformamide was added and the solution was kept at 20° C. The pH of this solution was 7.9. To this solution was added 2910 mg of mesyl compound with the aid of 5 ml of N,N-dimethylformamide. With the progress of the reaction, a white precipitate separated out. After 20 hours of reaction, the reaction mixture was analyzed by HPLC. The yield of the S-phenyl-L-cysteine derivative was 2894 mg (96%), the yield of the S-phenyl-D-cysteine derivative was 128 mg (4%), and the optical purity was 91.5% ee. The dehydroalanine derivative was not detected, and SN2:E2 =92:8.

EXAMPLE 3

Under nitrogen gas at room temperature, 3.83 ml of 1N-sodium hydroxide/H$_2$O and 1.5 ml of distilled water were added to 449 mg of thiophenol and the mixture was stirred for 30 minutes. Then, 5 ml of N,N-dimethylformamide was added and the solution was kept at 20° C. The pH of the solution at this stage was 8.8. To this solution was added 973 mg of mesyl compound. With the progress of the reaction, a white precipitate separated out. The reaction was continued for a total of 15 hours, at the end of which time 2 ml of distilled water was added. The pH of the solution at this stage was 8.1. A small sample of the reaction slurry was taken out and analyzed by HPLC. As a result, the dehydroalanine derivative was not detected. The molar ratio of the S-phenyl-L-cysteine derivative plus S-phenyl-D-cysteine derivative to the mesyl compound was 99:1 and the optical purity was 92.1 ee. The solution was then cooled to about 0° C., stirred for 30 minutes, and filtered. The net yield of the S-phenyl-L-cysteine derivative obtained as a solid was 936 mg (92%), and its optical purity was 91.9% ee.

The 400 MHz nuclear magnetic resonance spectrum of the N-benzyloxycarbonyl-S-phenyl-L-cysteine methyl ester thus obtained was as follows. (CDCl$_3$, TMS internal standard) δ: 3.36 to 3.45 (2H, m), 3.53 (3H, s), 4.61 to 4.65 (1H, m), 5.03 to 5.10 (2H, ABg, J=12.5 Hz), 5.60 to 5.62 (1H, b), 7.17 to 7.45 (10OH, m).

EXAMPLE 4

Under nitrogen gas at room temperature, 1 ml of distilled water and 286 mg of potassium bicarbonate were added to 346 mg of thiophenol and the mixture was stirred for 30 minutes. Then, 3 ml of N,N-dimethylformamide was added and the solution was kept at 20° C. To this solution was added 931 mg of N-benzyloxycarbonyl-o-tosyl-L-serine methyl ester with the aid of 2 ml of N,N-dimethylformamide. The reaction mixture was consistently slurry. After 17 hours of reaction, the reaction mixture was analyzed by HPLC. The yield of S-phenyl-L-cysteine derivative was 760 mg (95%) and that of S-phenyl-D-cysteine derivative was 21 mg (3%). The optical purity was 94.5% ee. The dehydroalanine derivative was not detected, and SN2:E2 =94:6.

Reference Example 1

Under nitrogen gas at room temperature, 125 mg of sodium hydride (content 67.4%) was added to a solution of 399 mg of thiophenol in 3 ml of N,N-dimethylformamide and the mixture was stirred for 30 minutes. This solution was then kept at 20° C. To this solution was added 971 mg of mesyl compound with the aid of 2 ml of N,N-dimethylformamide. After 2 hours of reaction, a small sample of the reaction mixture wrs taken and analyzed by HPLC. As a result, the starting mesyl compound was not detected. The molar ratio of S-phenyl-L-cysteine derivative plus S-phenyl-D-cysteine derivative to dehydroalanine derivative was 89:11 and the optical purity was 75.3% ee. After a total of 20 hours of reaction, the reaction mixture was analyzed by HPLC.

The yield of S-phenyl-L-cysteine derivative was 557 mg (55%), that of S-phenyl-D-cysteine derivative was 139 mg (14%), and the optioal purity was 60.1% ee. The yield of dehydroalanine derivative was 22% and SN2:E2=46:54.

EXAMPLE 5

Under nitrogen gas at room temperature, 3.32 ml (1.1 equivalents based on mesyl compound) of 1N-sodium hydroxide/$H_2O$ and 2 ml of distilled water were added to 374 mg (1.1 equivalents based on mesyl compound) of thiophenol and the mixture was stirred for 30 minutes. Then, 47 mg (0.05 equivalent based on mesyl compound) of benzyltributylammonium chloride was added and the solution was kept at 10° C. To this solution was added a solution of 971 mg of mesyl compound in 10 ml of chlorobenzene en bloc, with the aid of 2 ml of chlorobenzene. After 4 hours of reaction at 10° C., the cooling bath was removed to allow the reaction system to return to room temperature spontaneously and the reaction was continued. Total reaction time was 17.5 hours. The reaction mixture was then analyzed.

As a result, the yield of S-phenyl-L-cysteine derivative was 886 mg (88%), that of S-phenyl-D-cysteine derivative was 40 mg (4%), and the optical purity was 91.3% ee. The yield of dehydroalanine derivative was 7% and SN2:E2= 85:15.

EXAMPLES 6 to 13

Except that the reaction charge recipe and reaction conditions were changed to those indicated in Table 1, the reaction procedure of Example 5 was otherwise repeated. The results are presented in Table 2.

TABLE 1

| Example | Organic solvent Species | Amount[1] | Base Species | Eq[3] | PhSH Eq[2] | Phase transfer catalyst Species[3] | Eq[2] | Additive | Mode of Addition: | Reaction Condition |
|---|---|---|---|---|---|---|---|---|---|---|
| 6 | Ethyl acetate | 12 | NaOH | 1.10 | 1.10 | BTBAC | 0.05 | None | Mesyl compound + organic solvent | 25° C. 16 h |
| 7 | Dichlorobenzene | 10 | NaOH | 1.20 | 1.24 | BTBAC | 0.05 | None | PhSH + NaOH + $H_2O$ | 10° C. 17 h |
| 8 | Methylene Chloride | 10 | NaOH | 2.20 | 2.27 | BTBAC | 0.05 | None | NaOH + $H_2O$ | 0° C. 12 h |
| 9 | Methylene Chloride/Chlorobenzene | 5/5 | NaOH | 2.20 | 2.27 | BTBAC | 0.05 | None | NaOH + $H_2O$ | 0° C. 12 h |
| 10 | Chlorobenzene | 5 | $NaHCO_3$ | 1.10 | 1.15 | BTBAC | 0.05 | None | Mesyl compound + Organic solvent | 10° C. 16 h |
| 11 | Chlorobenzene | 5 | NaOH | 1.10 | 1.15 | TOMAC | 0.05 | None | Mesyl compound + Organic solvent | 10° C. 3 h |
| 12 | Chlorobenzene | 5 | NaOH | 1.10 | 1.15 | BTBAC | 0.05 | NaCL (4.4 eq) | Mesyl compound + Organic solvent | 10° C. 9 h |
| 13 | Chlorobenzene | 5 | NaOH | 1.10 | 1.15 | BTBAC | 0.05 | Sodium Hydrosulfite (0.05 eq) | Mesyl compound + organic solvent | 10° C. 16 h |

[1] the amount of solvent (ml) per g mesyl compound
[2] mol per mol mesyl compound
[3] BTBAC: benzyltributylammonium chloride
TOMAC: trioctylmethylammonium chloride

TABLE 2

| | Yield (%) | | | | | |
|---|---|---|---|---|---|---|
| Example | S-phenyl-L-Cysteine Derivatives | S-phenyl-D-Cysteine Derivatives | Dehydroalanine derivatives | Optical Purity (% ee) | Reaction Selectivity SN2:H2 | Remarks |
| 6 | 81 | 7 | 2 | 85 | 83:17 | |
| 7 | 96 | 6 | 5 | 89 | 84:16 | |
| 8 | 83 | 1 | 5 | 98 | 93:7 | |
| 9 | 90 | 4 | 2 | 92 | 90:10 | |
| 10 | 90 | 4 | 6 | 92 | 86:14 | |
| 11 | 90 | 6 | 5 | 88 | 84:16 | |
| 12 | 88 | 4 | 6 | 92 | 86:14 | |
| 13 | 89 | 4 | 5 | 92 | 87:13 | The amount of the byproduct didulfide was decreased |

EXAMPLE 14

Under nitrogen gas at room temperature, 10 ml of toluene was added to 2.82 g of N-benzyloxycarbonyl-L-serine methyl ester and the mixture was stirred until the solid dissolved. To this solution under stirring were added 1.91 g of methanesulfonyl chloride and 1.32 g of pyridine, and the reaction was carried out at about 30° C. for about 12 hours. Thereafter, 20 ml of ethyl acetate was added to this solution at room temperature and the mixture was washed with 10 ml of water, 10 ml of 1N-hydrochloric acid, 10 ml of saturated sodium bicarbonate/H$_2$O, and 10 ml of 15% sodium chloride/H$_2$O. The organic layer was then concentrated under reduced pressure and 15 ml of N,N-dlmetnylformamide (briefly DMF) was added to prepare a DMF solution of N-benzyloxycarbonyl-o-mesyl-L-serine methyl ester (hereinafter referred to briefly as mesyl compound). On the other hand, 15 ml of distilled water and 1.54 g of sodium hydrogencarbonate were added to 1.41 g of thiophenol under nitrogen gas at room temperature and the mixture was stirred for 30 minutes. Then, the above solution of mesyl compound was added and the mixture was stirred at about 20° C. With the progress of the reaction, a white precipitate separated out. After about 20 hours of reaction, the reaction mixture was analyzed.

As a result, the yield of S-phenyl-L-cysteine derivative was 3.50 g (91%), that of S-phenyl-D-cysteine derivative was 0.18 g (4.7%), and the optical purity was 90.2% ee. The dehydroalanine derivative was not detected and SN2:E2 =90:10.

Industrial Applicability

The method of producing a cysteine derivative according to the invention being as described above, it is economically advrntageous, because it provides for a high production efficiency even in a commercial-scale operation, and in particular, a high optical purity.

We claim:
1. A method comprising reacting an amino acid derivative of the following general formula (I):

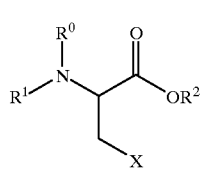
(I)

(wherein R$^1$ represents an amino-protective group; R$^0$ represents hydrogen or, taken together with R$^1$, represents an amino-protecting group; R$^2$ represents a carboxy-protecting group; X represents a leaving group) with a thiol compound of the following general formula (II):

R$^3$SH  (II)

(wherein R$^3$ represents an alkyl group of 1 to 7 carbon atoms, an aryl group of 6 to 10 carbon atoms, or an aralkyl group of 7 to 10 carbon atoms) to give a cysteine derivative of the following general formula (III):

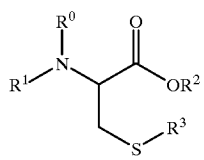
(III)

(wherein R$^0$, R$^1$, R$^2$, and R$^3$ are as defined above), wherein the reaction is conducted in the presence of a base and water in an organic reaction solvent.

2. A method of producing a cysteine derivative according to claim 1 wherein the base is a metal or ammonium hydroxide, carbonate, bicarbonate, acetate or hydrogenphosphate.

3. A method of producing a cysteine derivative according to claim 1, wherein the base is at least one member selected from the class consisting of sodium hydroxide, sodium bicarbonate, and potassium bicarbonate.

4. A method of producing a cysteine derivative according to claim 1, wherein the reaction is carried out at pH 3 to 11.

5. A method of producing a cysteine derivative according to claim 1, wherein X represents an alkylsulfonyloxy group of 1 to 10 carbon atoms, an arylsulfonyloxy group of 6 to 10 carbon atoms, or an aralkyloulfonyloxy group of 7 to 10 carbon atoms.

6. A method of producing a cysteine derivative according to claim 5 wherein X is tosyloxy or mesyloxy.

7. A method of producing a cysteine derivative according to claim 1, wherein R$^3$ is phenyl group.

8. A method of producing a cysteine derivative according to claim 1, wherein R$^2$ is methyl group.

9. A method of producing a cysteine derivative according to claim 1, wherein R$^1$ is benzyloxycorbonyl group, t-butoxycarbonyl group, methoxycarbonyl group, or ethoxycarbonyl group.

10. A method of producing a cysteine derivative according to claim 1, wherein the amino acid derivative of general formula (I) is an optically active compound which is either D-form or L-form.

11. A method of producing a cysteine derivative according to claim 1, wherein the organic reaction solvent is a solvent capable of forming a homogeneous phase with water.

12. A method of producing a cysteine derivative according to claim 11 wherein the water is used in an amount not exceeding 5 times the amount of the organic reaction solvent on a volume-to-volume basis.

13. A method of producing a cysteine derivative according to claim 11 wherein the organic reaction solvent is a solvent containing at least one of N,N-dimethylformamide and dimethyl sulfoxide.

14. A method of producing a cysteine derivative according to claim 11, wherein R$^1$ is benzyloxycarbonyl group; R$^2$ is methyl group; R$^3$ is phenyl group; the organic reaction solvent is a solvent containing N,N-dimethylformamide; and the water is used in an amount equal to $\frac{1}{20}$ through 5 times the amount of said organic reaction solvent on a volume-to-volume basis.

15. A method of producing a cysteine derivative according to claim 1, wherein the organic reaction solvent is a solvent capable of forming a heterogeneous phase with water.

16. A method of producing a cysteine derivative according to claim 15 wherein the water and the organic reaction solvent are used in a volume-to-volume ratio of 1:100 through 10:1.

17. A method of producing a cysteine derivative according to claim 15 wherein the organic reaction solvent is a halogenated hydrocarbon.

18. A method of producing a cysteine derivative according to claim 17 wherein the organic reaction solvent is at least one member selected from the group consisting of methylene chloride, chlorobenzene, and dichlorobenzene.

19. A method of producing a cysteine derivative according to claim 15, wherein a phase transfer catalyst is used.

20. A method of producing a cysteine derivative according to claim 19 wherein the phase transfer catalyst is at least one member selected from the group consisting of benzyltributylammonium chloride, tetrabutylammonium hydrogensulfate, trioctylmethylammonium chloride, and tetrabutylphosphonium bromide.

21. A method of producing a cysteine derivative according to claim 1, wherein the amino acid derivative of general formula (I) is prepared by introducing a leaving group X into the OH group of a serine derivative of the following general formula (VI):

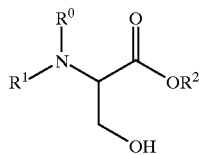

(VI)

(wherein $R^1$ represents an amino-protecting group; $R^0$ represents hydrogen or, taken together with $R^1$, represents an amino-protecting group; $R^2$ represents a carboxy-protecting group).

22. A method of producing a cysteine derivative according to claim 21 wherein the procedure of introducing the leaving group X into the serine derivative of general formula (VI) and then reacting the derivative with the thiol compound of general formula (II) to give the cysteine derivative or general formula (III) is carried out without isolation of the amino acid derivative of general formula (I).

23. A method of producing a cysteine derivative according to claim 21 wherein the leaving group X is tosyloxy group or mesyloxy group; the thiol compound of general formula (II) is thiophenol; and the solvent for use in introducing the leaving group is at least one kind selected from the group consisting of methylene chloride, toluene, and chlorobenzene.

* * * * *